US00PP28977P3

(12) United States Plant Patent
Shock et al.

(10) Patent No.: US PP28,977 P3
(45) Date of Patent: Feb. 20, 2018

(54) ***STEVIA* PLANT NAMED 'SW 227'**

(50) Latin Name: *Stevia rebaudiana*
Varietal Denomination: SW 227

(71) Applicant: S&W Seed Company, Fresno, CA (US)

(72) Inventors: Clinton C. Shock, Ontario, OR (US); Cheryl A. Parris, Ontario, OR (US)

(73) Assignee: S&W Seed Company, Sacramento, CA (US)

( * ) Notice: Subject to any disclaimer, the term of this patent is extended or adjusted under 35 U.S.C. 154(b) by 7 days.

(21) Appl. No.: 14/999,118

(22) Filed: Mar. 31, 2016

(65) Prior Publication Data

US 2017/0290225 P1 Oct. 5, 2017

(51) Int. Cl.
*A01H 5/04* (2006.01)

(52) U.S. Cl.
USPC ..... Plt./258

(58) Field of Classification Search
USPC ..... Plt./258, 263.1
See application file for complete search history.

(56) References Cited

U.S. PATENT DOCUMENTS

| | | | |
|---|---|---|---|
| PP10,562 | P | 8/1998 | Sys et al. |
| PP10,563 | P | 8/1998 | Brandle et al. |
| PP10,564 | P | 8/1998 | Marsolais et al. |
| 6,031,157 | A | 2/2000 | Morita et al. |
| 6,080,561 | A | 6/2000 | Morita et al. |
| 6,255,557 | B1 | 7/2001 | Brandle |
| 7,862,845 | B2 | 1/2011 | Magomet et al. |
| 7,884,265 | B2 | 2/2011 | Morita et al. |
| PP22,593 | P3 | 3/2012 | Garnighian |
| PP23,164 | P3 | 11/2012 | Britos |
| PP23,728 | P3 | 7/2013 | Britos |
| 2009/0214753 | A1 | 8/2009 | Morita et al. |
| 2011/0023192 | A1 | 1/2011 | Morita et al. |
| 2011/0195169 | A1 | 8/2011 | Markosyan et al. |
| 2011/0271413 | P1 | 11/2011 | Gamighian |
| 2012/0058247 | A1 | 3/2012 | Shi |
| 2012/0090062 | P1 | 4/2012 | Alvarez |
| 2013/0347140 | A1 | 12/2013 | Wang |
| 2016/0057955 | A1 | 3/2016 | Li et al. |
| 2016/0057965 | A1 | 3/2016 | Li et al. |
| 2016/0057966 | A1 | 3/2016 | Li et al. |
| 2016/0165777 | P1 | 6/2016 | Warner et al. |
| 2016/0165778 | P1 | 6/2016 | Warner et al. |
| 2016/0165779 | P1 | 6/2016 | Warner et al. |

OTHER PUBLICATIONS

Ahmed et al., An Efficient Method for in vitro Clonal Propagation of a Newly Introduced Sweetener Plant (*Stevia rebaudiana* Bertoni.) in Bangladesh, American-Eurasian Journal of Scientific Research 2(2):121-125 (2007).

Akita et al., Mass propagation of shoots of *Stevia rebaudiana* using large scale bioreactor, Plant Cell Reports 13:180-183 (1994).

Ali et al., Biochemical Investigation During Different Stages of in Vitro Propagation of *Stevia rebaudiana*, Pak. J. Bot., 42(4): 2827-2837 (2010).

Anbazhagan et al., In vitro production of *Stevia rebaudiana* Bertoni, Emir. J. Food Agric. 22(3):216-222 (2010).

Brandle et al., *Stevia rebaudiana:* Its agricultural, biological, and chemical properties, Can. J. Plant Sci. 78:527-536 (1998).

Brandle and Telmer et al., Steviol glycoside biosynthesis, Phytochemistry 68:1855-1863 (2007).

Dacome et al., Sweet diterpenic glycosides balance of a new cultivar of *Stevia rebaudiana* (Bert.) Bertoni: Isolation and quantitative distribution by chromatographic, spectroscopic, and electrophoretic methods, Process Biochemistry 40:3587-3594 (2005).

Debnath, Clonal propagation and antimicrobial activity of an endemic medicinal plant *Stevia rebaudiana*, Journal of Medicinal Plants Research 2(2):045-051 (2008).

Goettemoeller and Ching, Seed Germination in *Stevia rebaudiana,* J. Janick (ed), ASHS Press (1999), pp. 510-511.

Henderson, Jr. and Berry, Isocratic *Stevia* Sweetener Analysis using Selective ZORBAX Columns: Application Note—Food, www.agilent.com/chem, Agilent Technologies, Inc. 5990-3933EN (Apr. 30, 2009), pp. 1-6.

Jena et al., Effect of phytoregulators on in vitro mass propagation of *Stevia rebaudiana* Bertoni, International Journal of Integrative Biology, 8(1):56-59 (2009).

Kolb et al., Analysis of Sweet Diterpene Glycosides from *Stevia rebaudiana:* Improved HPLC Method, J. Agric. Food Chem. 49:4538-4541 (2001).

Madan et al., *Stevia rebaudiana* Bertoni—A Review, Indian Journal of Natural Products and Resources 1(3):267-286 (2010).

Midmore and Rank, A new rural industry—*Stevia*—to replace imported chemical sweeteners, Rural Industries Research and Development Corporation, Publication No. W02/022 (Aug. 2002), pages 1-23.

Reick et al., Improved HPLC method for the evaluation of the major steviol glycosides in leaves of *Stevia rebaudiana*, Eur. Food Res. Technology 231:581-588 (2010).

Sharma et al., Chemistry and in vivo profile of ent-kaurene glycosides of *Stevia rebaudiana* Bertoni—An overview, Natural Product Radiance 8(2):181-189 (2009).

Shatnawi et al., Clonal propagation and cryogenic storage of the medicinal plant *Stevia rebaudiana*, Spanish Journal of Agricultural Research 9(1):213-220 (2011).

Shimadzu, Analysis of Steviol Glycosides in *Stevia* Extract, Shimadzu Corporation Application News, No. L439 (2012).

Shock, Experimental Cultivation of Rebaudi's *Stevia* in California, University of California Davis, Agronomy Progress Report No. 122 (Apr. 1982).

Shock, Rebaudi's *Stevia*: natural noncaloric sweeteners, California Agriculture 36(9) and (10), University of California Davis, Division of Agricultural Sciences Reports of Progress in Research (Sep.-Oct. 1982).

(Continued)

*Primary Examiner* — Susan McCormick Ewoldt
(74) *Attorney, Agent, or Firm* — Karen Canaan; CanaanLaw, P.C.

(57) ABSTRACT

A new and distinct *Stevia rebaudiana* plant named 'SW 227' is described. The new variety is distinguished from other *Stevia* varieties by high plant vigor characterized by plant anatomy with extensive stooling and branching; an excellent sweet leaf taste with very low bitterness and aftertaste; and leaves having a rebaudioside A content of 10.7%. Samples have been collected with total steviol glycoside content of 13.3%.

6 Drawing Sheets

(56) References Cited

OTHER PUBLICATIONS

Tavarini and Agnelini, *Stevia rebaudiana* Bertoni as a source of bioactive compounds: the effect of harvest time, experimental site and crop age on steviol glycoside content and antioxidant properties, J. Sci. Food. Agric. 93:2121-2129 (2013).
Taware et al., Comparative studies of in vitro and in vivo grown plants and callus of *Stevia rebaudiana* (Bertoni), International Journal of Integrative Biology 9(1):10-15 (2010).
Yadav et al., A review on the improvement of *Stevia* [*Stevia rebaudiana* (Bertoni)], Can. J. Plant Sci. 91:1-27 (2011).
International Search Report and Written Opinion for commonly owned PCT/US2015/060925 dated Jan. 29, 2016.
International Search Report and Written Opinion for commonly owned PCT/US2015/061185 dated Feb. 1, 2016.
S&W Press Release for SW 107 Varietal dated Dec. 1, 2014 (the SW 107 Varietal was filed as Plant U.S. Appl. No. 14/544,136 on Nov. 30, 2014).
International Search Report and Written Opinion for counterpart PCT/US2017/023231 dated Jun. 16, 2017.

*STEVIA* PLANT NAMED 'SW 227'

Genus and species: *Stevia rebaudiana.*
Variety denomination: 'SW 227'.

BACKGROUND OF THE INVENTION

*Stevia rebaudiana* is a plant species in the sunflower (Asteraceae) family, which has naturally sweet leaves. The active compounds that impart the sweet flavor to *stevia* leaves are steviol glycosides. The most common steviol glycosides are stevioside and rebaudioside A, both of which have up to 250 to 400 times the sweetness of sugar. Stevioside tends to be more prevalent in unimproved lines of *stevia* leaves than rebaudioside A. The development of new varieties of *Stevia rebaudiana* with higher levels of rebaudioside A than stevioside is desirable for use as a sugar substitute.

The present invention relates to a new and distinct variety of *Stevia rebaudiana,* the 'SW 227' line, which has high plant vigor characterized by extensive stooling and branching; an excellent sweet leaf taste with very low bitterness and aftertaste; and leaves having an average rebaudioside A content of 10.7%. Table 1 provides averaged stevioside data for samples of the dry leaves of the 'SW 227' line.

Plant Vigor: The 'SW 227' line was found to have much greater stooling (branching from the ground) and much greater branch numbers in comparison to the majority of the plant population from which the line was derived.

Leaf Taste: The leaves of the 'SW 227' line were found to have an excellent sweet taste in comparison to a majority of the plant population from which the line was derived and very little bitterness and aftertaste in comparison to most *stevia* varieties.

Dry Leaf Yield: The 'SW 227' line producing 5500 kg/ha (~4907 lb/ac) of dry leaf yield based on six months growth (April to September) at Ontario, Oreg., USA in 2015.

Rebaudioside A content: In 2015, the leaves of the 'SW 227' line were found to have a high percentage of rebaudioside A at 10.7% (Table 1).

Stevioside content: The leaves of the 'SW 227' line were found to have a low percentage of stevioside at just 1.4% (Table 1).

Steviol Glycosides: The leaves of the 'SW 227' line were found to have high levels of total steviol glycosides at 13.3%, with rebaudioside A accounting for 80.4% of the total steviol glycoside content in the leaves (Table 1).

Ratio of rebaudioside A to stevioside content: The ratio of rebaudioside A to stevioside in the leaves of the 'SW 227' line was found to be high at 7.6 (Table 1).

TABLE 1

| Dry Leaves | 'SW 227' |
|---|---|
| Percentage of rebaudioside A | 10.7% |
| Percentage of stevioside | 1.4% |
| Percentage of total steviol glycosides | 13.3% |
| Ratio of rebaudioside A:stevioside | 7.6 |
| Percentage of rebaudioside A to total steviol glycosides | 80.4% |

The 'SW 227' *stevia* line was asexually reproduced from root cuttings derived from a single *Stevia rebaudiana* plant that was selected on Oct. 5, 2014, at Ontario, Oreg. and which was grown outdoors under full sunlight. The parent plant was grown in 2013 from seed derived from a cross between the *Stevia rebaudiana* clone known as 'selection 395' (unpatented) and the 'SW 129' *stevia* line (U.S. Plant Pat. No. 28,373).

The selection of the 'SW 227' line was based on evaluations of plant vigor, particularly plant stooling and branching; leaf taste; and rebaudioside A content.

The 2015 leaf harvest period in Ontario, Oreg. for the 'SW 227' line was a single harvest in the fall or multiple harvests throughout the summer to early fall. Plant yield and leaf quality of the 'SW 227' line was confirmed throughout 2015 in Ontario, Oreg.

BRIEF SUMMARY OF THE INVENTION

The following characteristics of the new 'SW 227' line have been repeatedly observed and can be used to distinguish the 'SW 227' line as a new and distinct cultivar of a *Stevia* plant:

1. Exceptional stooling and branching morphology of the plant
2. High plant vigor;
3. High plant yield;
4. Late flowering;
5. Excellent sweet flavor to the leaves with very little bitterness and aftertaste;
6. Leaves having an average rebaudioside A content measured at 10.7%;
7. Leaves having an average stevioside content measured at 1.4%;
8. Leaves having an average ratio of rebaudioside A to stevioside of measured at 7.6;
9. Leaves having an average total steviol glycoside content measured at 13.3%;
10. Leaves having an average percentage of rebaudioside A to total steviol glycosides measured at 80.4%; and
11. Approximately 5500 kg/ha of dry leaf yield based upon six months of growth at Ontario, Oreg., in 2015.

BRIEF DESCRIPTION OF THE DRAWINGS

The accompanying photographs show, as nearly true as is possible in color illustrations of this type, typical flower and foliage characteristics of the 'SW 227' line. The plants depicted in the accompanying photographs are approximately one year old.

DETAILED BOTANICAL DESCRIPTION

When compared to its parent lines, the 'SW 227' line has a lower percentage of stevioside (1.4% for 'SW 227' versus 2.12% for 'SW 129' and 2.26% for 'selection 395') resulting in reduced bitterness and aftertaste for the 'SW 227' line versus the parent 'SW 129' and 'selection 395' lines. When the leaves of the 'SW 227' line were compared to *stevia* leaves grown from commercially available *stevia* seeds, the leaves of the 'SW 227' line were sweeter and less bitter than the leaves grown from the commercial seed.

Following is a detailed botanical description of a new and distinct variety of a *Stevia* plant known as 'SW 227.' Plant observations were made October 2015, on mature one year old plants grown in a field in Ontario, Oreg. in natural light. The 'SW 227' line has not been observed under all possible environmental conditions. Where characteristics, such as dimensions, sizes, colors, and other such characteristics are given, it is to be understood that such characteristics are approximations or averages and that such approximations are not intended to be limiting. It is also to be understood that the phenotype of the variety may be altered by changes with environment, such as season, temperature, light quality, light intensity, day length, cultural conditions, and the like. Color notations are based on *The Royal Horticultural Society Colour Chart,* The Royal Horticultural Society, London, 2007.

Botanical classification: *Stevia rebaudiana* cultivar 'SW 227'.

Parentage: 'SW 227' *stevia* line was derived from a 2013 cross between the *Stevia rebaudiana* clone known as 'selection 395' (unpatented) and the 'SW 129' *stevia* line (patented).

*Seed parent.*—'Selection 395' cloned by Clinton C. Shock and rooted in Ontario, Oreg.

*Pollen parent.*—'SW 129' *stevia* line described and claimed in commonly owned U.S. Plant Pat. No. 28,373.

Figure 1:
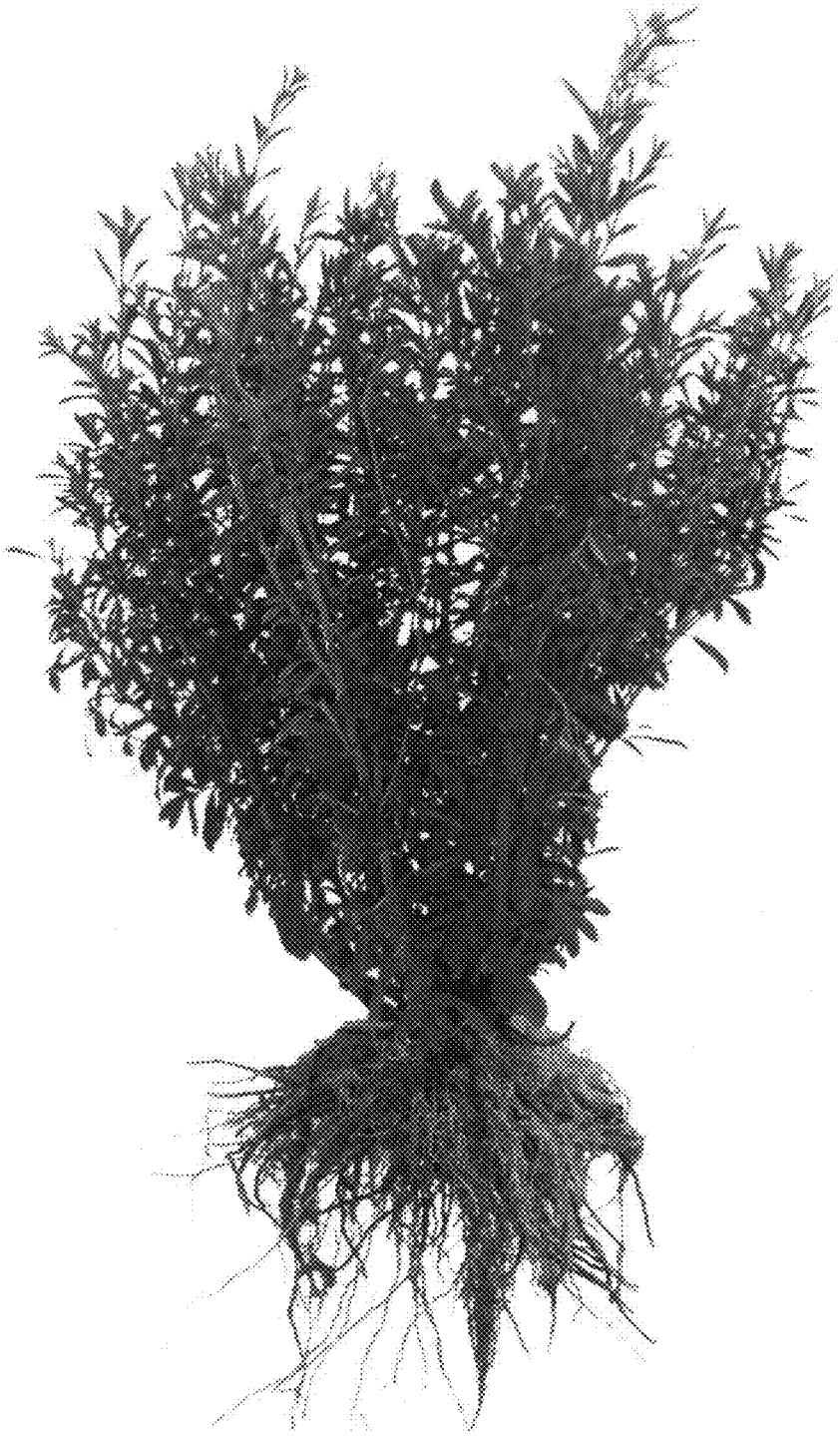
FIG. 1 is a color photograph of a fully mature 'SW 227' *Stevia* plant near the end of the plant's first growing season. The photograph shows the plant from roots to top of the plant.
Figure 2:
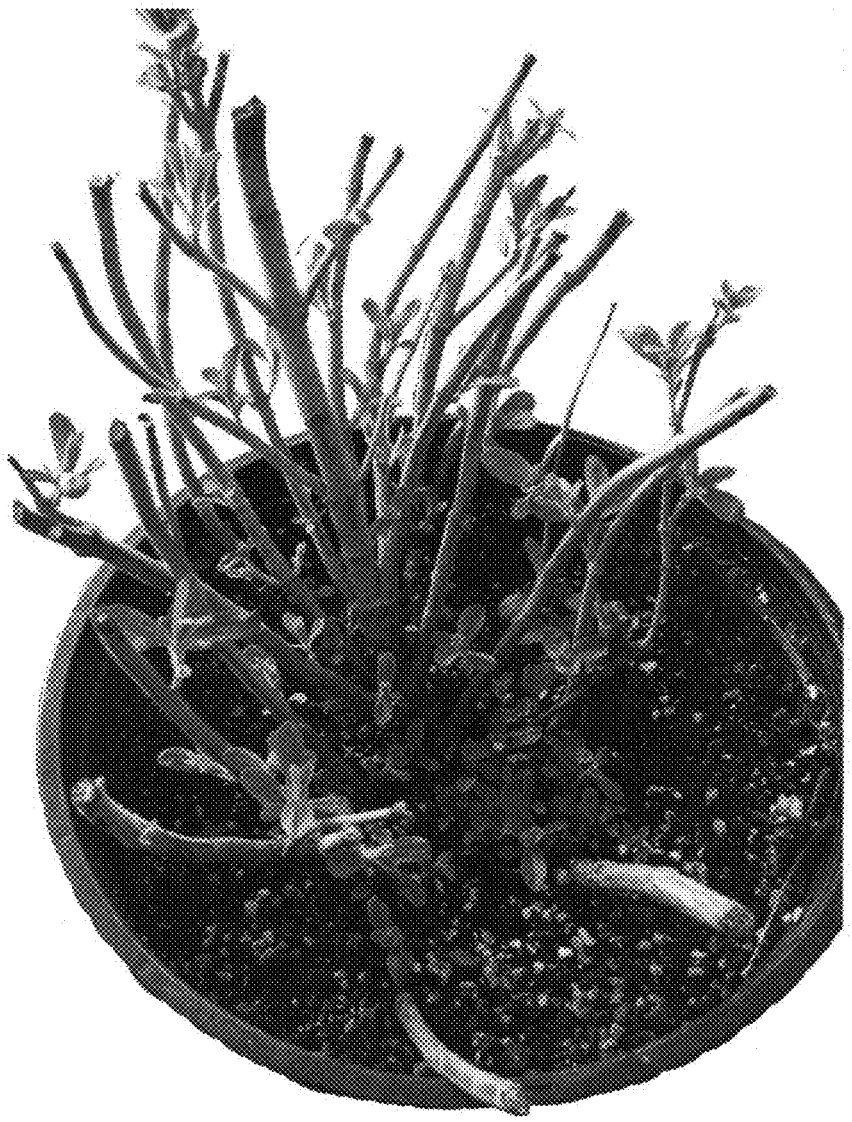
FIG. 2 is a color photograph of a top view of a 'SW 227' *Stevia* plant. The photograph shows the plant's strong stooling habit.
Figure 3:
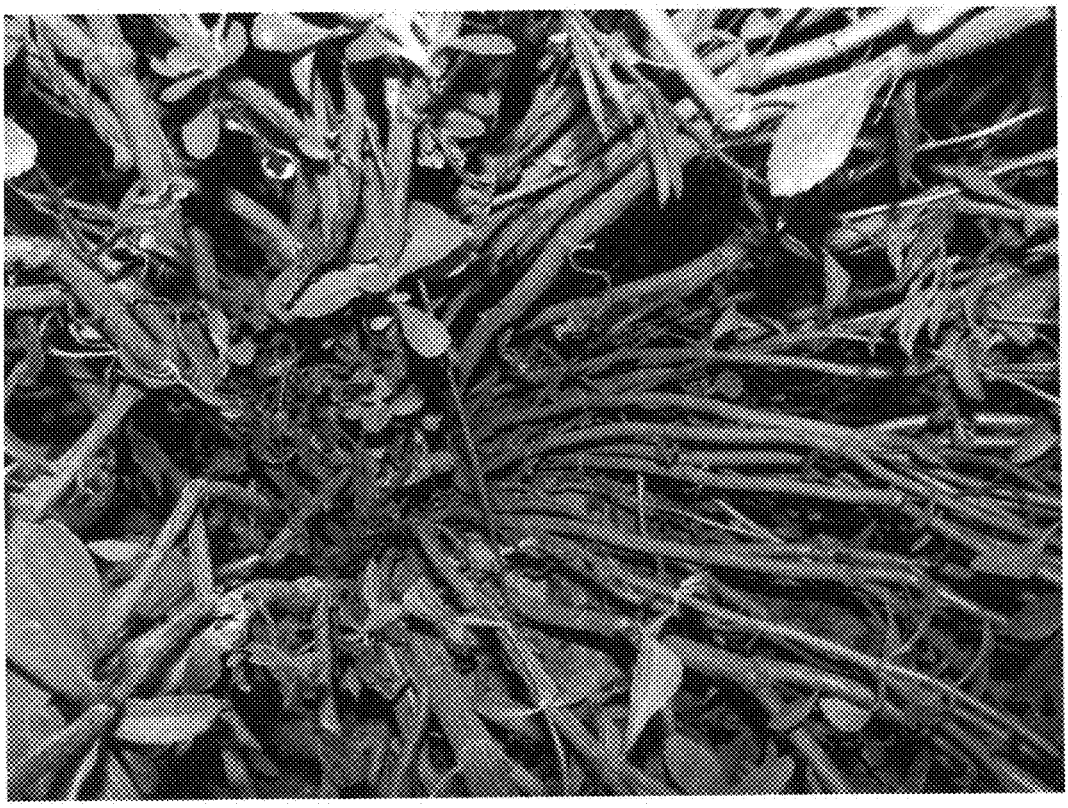
FIG. 3 is a color photograph of a top view of a 'SW 227' *Stevia* plant. The photograph shows the plant's extensive branching.

Plant (description based on FIGS. 1, 2, and 3):

*Type.*—Perennial in climates with mild winter temperatures.

*Form and habit.*—Multiple branching bush.

*Height (from top of soil).*—75 cm.

*Width (including flowers).*—60 cm.

*Number of nodes on main stem.*—Varies.

*Stooling.*—Prolific branch generation from subsurface root material.

*Root initiation.*—8 days.

Plant (description based on FIGS. 2 and 3):

*Number of basal buds.*—Many.

*Harvest cycle.*—Single fall or multiple throughout the summer to early September.

Figure 4:
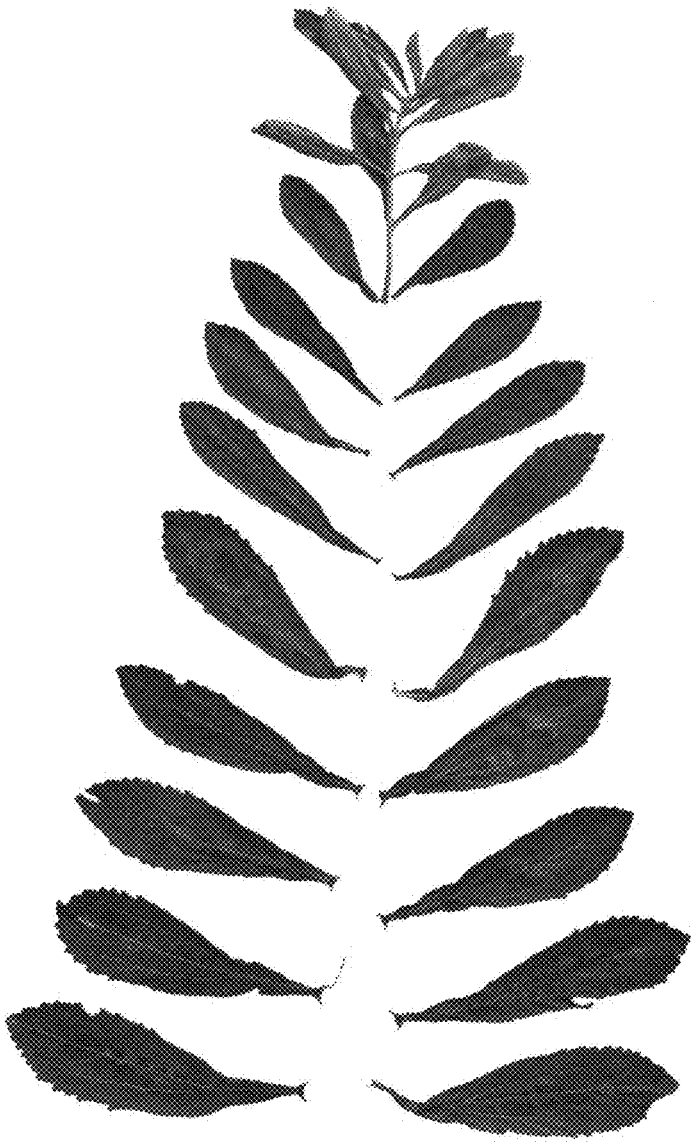
FIG. 4 is a color photograph of the leaves of a 'SW 227' *Stevia* plant
Figure 5:
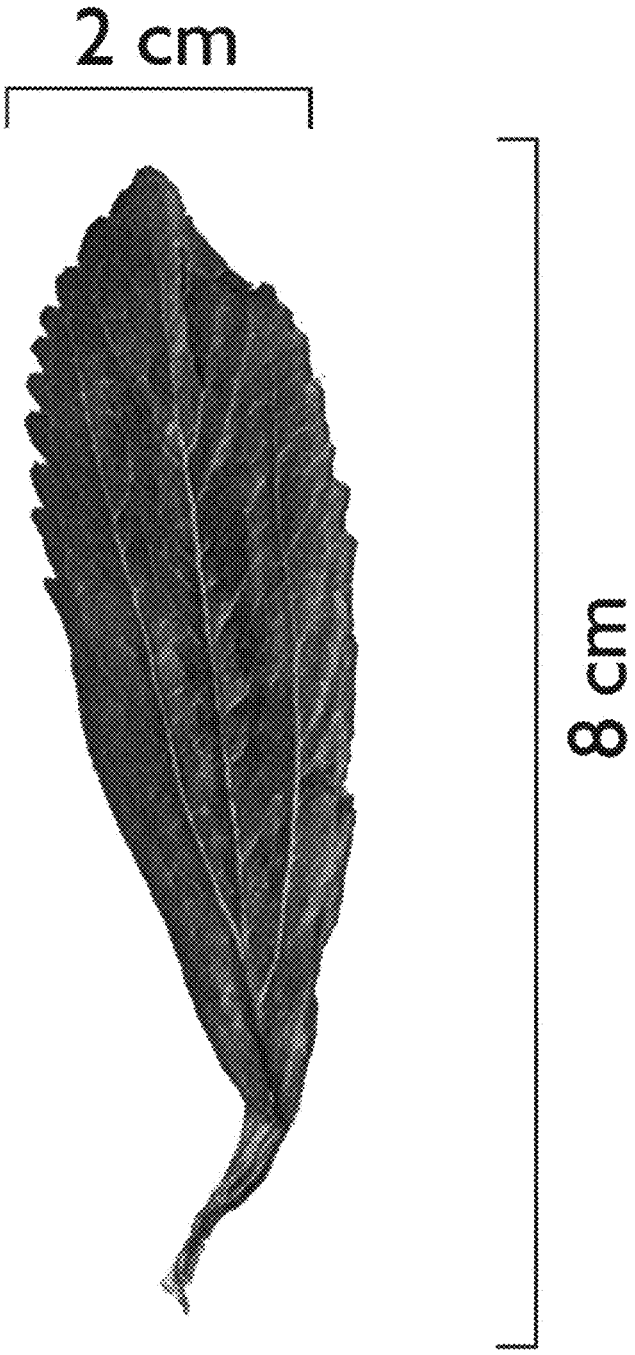
FIG. 5 is a color photograph of a single leaf of a 'SW 227' *Stevia* plant. The photograph includes the dimensions of the leaf.

Leaves (description based on FIGS. 4 and 5):

*Length.*—~8 cm.

*Width.*—~2 cm.

*Arrangement.*—Opposite.

*Shape.*—Lanceolate, with 0.5 mm to 1.0 mm serrations ⅓ the length of a leaf.

*Apex descriptor.*—Acute.

*Base descriptor.*—Cuneate.

*Margin descriptor.*—Crenate.

*Venation pattern.*—Longitudinal.

*Color, mature foliage.*—Upper surface. RHS137C. Lower surface. RHS137C.

*Color; veins.*—RHS 139C.

*Texture, mature foliage.*—Upper surface. Smooth. Lower surface. Slight pubescence.

*Petiole length.*—~0.2 cm.

*Petiole diameter.*—~0.02 cm.

*Petiole texture.*—Upper surface: Slight pubescence. Lower surface: Slight pubescence.

*Pubescence color.*—Upper surface. RHS 139C. Lower surface. RHS 139C.

*Stevioside content.*—1.4%.

*Rebaudioside A content.*—10.7%, with up to 14.3% observed.

*Rebaudioside A as a percentage of total steviol glycosides.*—80.4%.

*Ratio of rebaudioside A to stevioside.*—7.6.

*Total steviol glycosides.*—13.3%, with up to 18.3% observed.

*Leaf harvest period.*—A single harvest in fall or multiple harvests throughout summer to early fall in Ontario, Oreg.

Stem:

*Length (excluding inflorescence).*—Varies to 75 cm.

*Diameter.*—Varies up to 1.5 cm.

*Texture.*—Pubescent.

*Color.*—RHS 145B.

Figure 6:
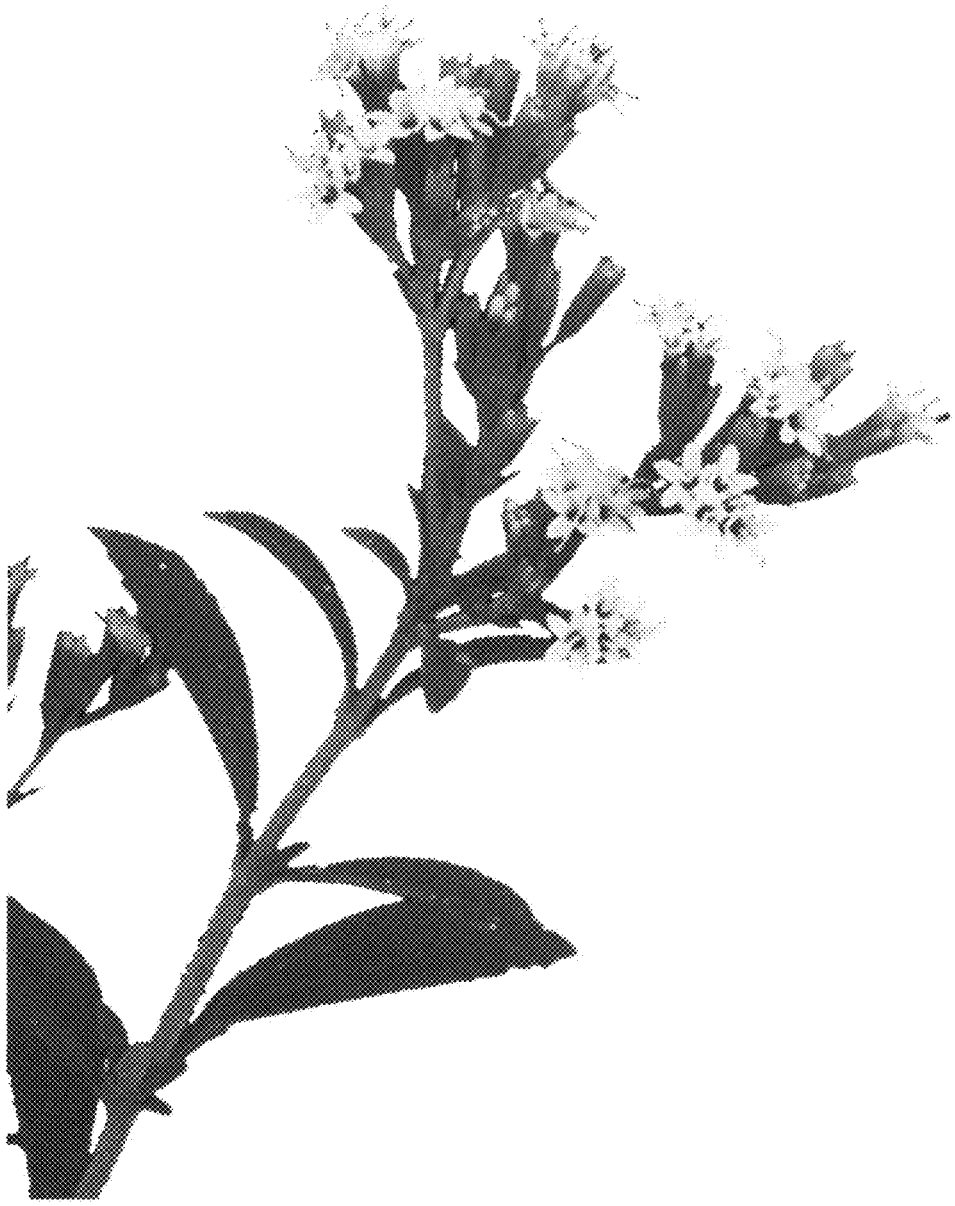
FIG. 6 is a color photograph of the flowers of an 'SW 227' *Stevia* plant.

Flowers (description based on FIG. 6):

*Inflorescence type.*—Panicle.

*Inflorescence width.*—Varies up to 15 cm.

*Petal color.*—RHS N155D.

*Petal length.*—~0.6 cm.

*Petal width.*—~0.1 cm.

*Bloom period.*—October to December at Ontario, Oreg., with protection from freezing weather required after September.

*Arrangement.*—Composite.

*Shape.*—Cluster.

*Fragrance.*—None.

*Number of flowers per capitulum.*—5.

*Average number of petals per flower.*—Sympetalous.

Peduncle:

*Color.*—RHS 145B.

*Diameter.*—~0.15 cm.

*Aspect.*—Perpendicular.

*Texture.*—Pubescent.

Pedicles:

*Color.*—RHS 145B.

*Diameter.*—~0.03 cm.

*Aspect.*—45 degrees.

*Texture.*—Pubescent.

Disc florets:

*Arrangement.*—Radially symmetrical.

*Shape.*—Tubular.

Phyllaries:

*Quantity.*—5.

*Length.*—~0.7 cm.

*Width.*—~0.15 cm.

*Shape.*—Lanceolate.

*Apex.*—Acute.

*Base.*—Fused.

*Margin.*—Overlapping.

*Color.*—RHS 145B.

Reproductive organs:

*Androecium.*—Stamen quantity. 5. Anther length. ~0.4 cm. Anther color. RHS 199A.

*Gynoecium.*—Pistil length. ~0.8 cm. Style color. RHS N155B. Stigma color. RHS N155B Fruit and seed set:

*Flowering.*—Later seed set compared to other known *stevia* lines.

*Seeds.*—Small black achene (~3.0 mm) with pappus (~4.0 mm) attached, typical of *Stevia rebaudiana.*

Cold hardiness: Hardy to −5° C. (23° F.) at Ontario, Oreg.

Heat tolerance: Hardy to a monthly average maximum temperature of 34° C. (93.2° F.) at Ontario, Oreg.

We claim:

1. A new and distinct cultivar of *Stevia* plant named 'SW 227' as substantially shown and described herein.

* * * * *